United States Patent
Bäther et al.

(10) Patent No.: US 6,348,355 B1
(45) Date of Patent: Feb. 19, 2002

(54) TESTING ELEMENT FOR THE COLORIMETRIC DETERMINATION OF OXIDIZABLE COMPONENTS IN GAS MIXTURES

(75) Inventors: Wolfgang Bäther, Lübeck; Ralf Miethchen; Alexej Miller, both of Rostock, all of (DE)

(73) Assignee: Dräger Sicherheitstechnik GmbH (DE)

( * ) Notice: Subject to any disclaimer, the term of this patent is extended or adjusted under 35 U.S.C. 154(b) by 0 days.

(21) Appl. No.: 09/407,541

(22) Filed: Sep. 28, 1999

(30) Foreign Application Priority Data

May 21, 1999 (DE) .......................... 199 23 424

(51) Int. Cl.[7] .............................. G01N 21/75
(52) U.S. Cl. .................. 436/167; 436/132; 436/134; 436/136; 436/169; 422/55; 422/57; 422/85; 422/87
(58) Field of Search .............. 422/59, 55, 57, 422/60, 85, 87; 436/68, 60, 132, 131, 134, 136, 164, 167, 169

(56) References Cited

U.S. PATENT DOCUMENTS

| | | | |
|---|---|---|---|
| 5,178,831 A | * 1/1993 | Sakota et al. | 422/56 |
| 5,290,683 A | * 3/1994 | Israel et al. | 435/26 |
| 5,518,891 A | * 5/1996 | Gibboni et al. | 435/28 |
| 5,550,032 A | * 8/1996 | Isbister et al. | 435/39 |

FOREIGN PATENT DOCUMENTS

| | | | |
|---|---|---|---|
| DE | 34 07 686 C1 | 7/1985 | |
| DE | 39 02 402 C1 | 6/1990 | |
| EP | 513594 | * 11/1992 | C12Q/1/26 |
| GB | 793727 | 4/1958 | |

* cited by examiner

Primary Examiner—Jill Warden
Assistant Examiner—Latoya I. Cross
(74) Attorney, Agent, or Firm—McGlew and Tuttle, P.C.

(57) ABSTRACT

A testing elements for the calorimetric determination of oxidizable gas and/or vapor components in gas mixtures is provided. The testing element contains, besides usual oxidizing agents, at least one redox indicator, which is in the oxidized form. The redox indicator is preferably a benzidine derivative according to the general formula

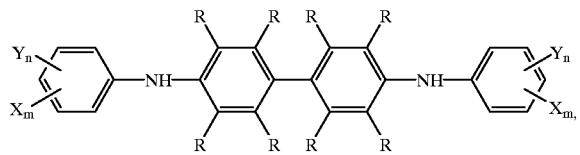

(I)

in which the radicals R are identical or different and denote a hydrogen, alkyl, aryl, halogen, trifluoromethyl, cyano, nitro, dialkylamino, ester, sulfoxyl ester, alkyloxy or aryloxy, X denotes a halogen, Y denotes a trifluoromethyl, cyano, nitro, dialkylamino, ester, sulfoxyl ester, alkyloxy or aryloxy, n is an integer from zero to three, and m equals 5−n. The testing elements are preferably designed as detector tubes that contain carrier materials, to which the oxidizing reagents and redox indicators are applied.

12 Claims, 1 Drawing Sheet

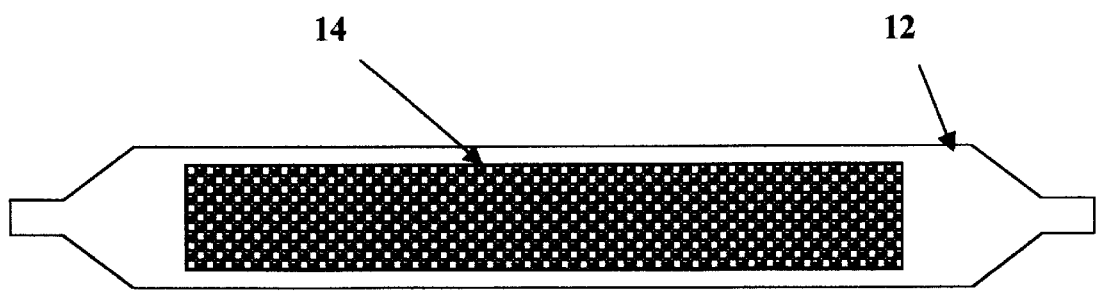

TESTING ELEMENT FOR THE COLORIMETRIC DETERMINATION OF OXIDIZABLE COMPONENTS IN GAS MIXTURES

FIELD OF THE INVENTION

The present invention pertains to testing elements for the colorimetric determination of oxidizable gas and/or vapor components in gas mixtures. The testing elements are usually designed as detector tubes, which contain carrier materials, to which at least one oxidizing agent is applied. The present invention also pertains to redox indicators that can be used in the testing elements, especially special benzidine derivatives.

BACKGROUND OF THE INVENTION

Various designs of colorimetric measuring systems, by means of which gases can be tested for components contained in them simply, rapidly and inexpensively, have been known. A device available as Alco-Check™ for the semi-dquantitative determination of the blood alcohol concentration from the alcohol content in the exhaled air is a known example. The breathing air is blown here through a detector tube containing chromosulfuiric acid on $SiO_2$. If the breathing air contains alcohol vapor, the color of the originally yellow substance of the detector tube changes to green as a consequence of the reduction into a chromium(III) compound. The lower detection limit is 0.3 promille.

As is shown by the above example, colorimetric measuring systems for gases usually comprise testing elements, preferably detector tubes, which contain reagents that are adsorbed on carrier substances and form colored reaction products with the gaseous or vapor substance to be tested, optionally by means of a catalyst. The intensity and the length of the colored zone make possible a qualitative or quantitative evaluation.

The automatic optoelectronic evaluation of the change in the color of the detector tube has been known from DE 39 02 402 C1.

Another testing element, in which the gas to be tested is drawn through an indicator strip, to has been known from DE 34 07 686 C1. The reagents on the indicator strip react specifically with the components of the sample to be determined. This leads to a change in color, which can be detected photometrically.

Another embodiment of such testing elements is that of a badge. A flat disk, e.g., a paper disk, impregnated with the reagent, reacts with the components of the air due to diffusion, while the color of the disk changes. The intensity of the change in color within a defined period of time is a measure of the concentration of the component present in the air.

The colorimetric measuring system used most frequently is based on redox reactions. A decisive requirement on the reagent system is the change in the intrinsic color with a sufficient color intensity during the reaction process. For example, the intrinsic color of the chromosulfuiric acid reagent system changes from yellow to green as a consequence of the reduction of chromium(VI) to chromium(III). Another example is the change in color from purple to yellowish brown in the permanganate system as a consequence of the reduction of Mn(VII) to Mn(IV).

However, the intensity of the intrinsic color is not very high in many reagent systems, or the maximum of the change in color is at a wavelength that can be read, e.g., optoelectronically, with difficulty only. Furthermore, there are a large number of reagent systems in which the intrinsic color changes only slightly if at all in the course of the reaction with the analyte, even though strong oxidizing agents are used.

Redox indicators, whose use depends on the change potential of the redox system, are used in titrimetric analysis in the liquid phase to better recognize or visualize the point of change. The examples of prior-art redox indicators include indigosulfonates, methylene blue, iodine-potassium iodide-starch, indophenols, diphenylbenzidine, triphenylmethane dyes, phenylanthranilic acid, Ferroin, and nitro-Ferroin.

However, most analytes (e.g., ethanol, gasoline hydrocarbons, carbon monoxide) require strong oxidizing agents, under the effect of which most of the known redox indicators are decomposed, so that these are not suitable for the purposes mentioned.

SUMMARY AND OBJECTS OF THE INVENTION

Thus, the basic object of the present invention is to provide testing elements whose indicator components are stable even in a strongly oxidizing matrix and, in particular, display an intense change in color intensity. Another object of the present invention is to provide redox indicators for this purpose, which are stable, in particular, even on prolonged storage in the oxidation matrix.

Testing elements containing a carrier material to which at least one oxidizing agent and at least one redox indicator are applied are provided according to the present invention to accomplish this object, the redox indicator being in the oxidized form.

The redox indicator is preferably a benzidine derivative according to the general formula

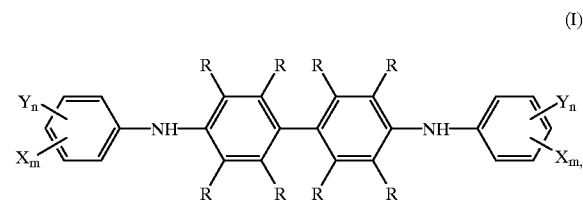

(I)

in which the radicals R are identical or different and denote a hydrogen, alkyl, aryl, halogen, trifluoromethyl, cyano, nitro, dialkylamino, ester, sulfoxyl ester, allyloxy or aryloxy, X denotes a halogen, Y denotes a trifluoromethyl, cyano, nitro, dialkylamino, ester, sulfoxyl ester, alkyloxy or aryloxy, n is an integer ranging from zero to three, and m equals 5–n.

R preferably denotes a hydrogen, n equals 1, and m equals 4. X preferably denotes a fluorine and Y preferably denotes a trifluoromethyl, cyano or nitro, Y denoting trifluoromethyl being most preferred.

The particularly preferred compounds are:

N,N'-Bis[2,3,5,6-tetrafluoro-4-(trifluoromethyl)-phenyl]-benzidine, (II)

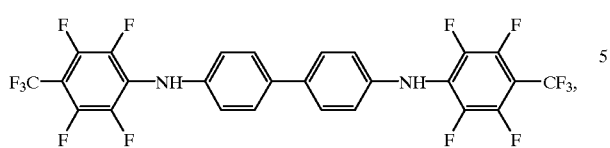

N,N'-bis[2,3,5,6-tetrafluoro-4-cyanophenyl]-benzidine, (III)

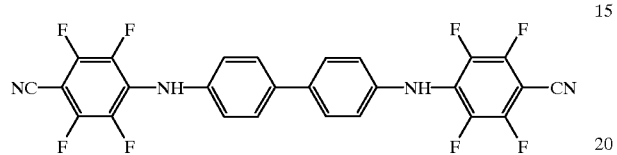

and N,N'-bis[2,3,5,6-tetrafluoro-4-nitrophenyl]-benzidine, (IV)

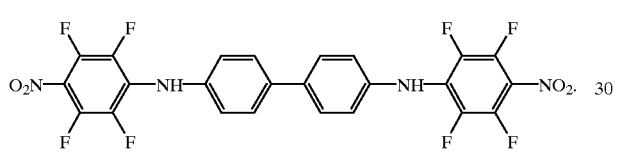

By selecting different substituents Y, which act as a donor or acceptor on the conjugated system, the change potential and/or the maximum of the absorption or remission wavelength can be influenced as desired. For example, the electron-attracting trifluoromethyl and nitro groups ensure a reduction in the change potential.

Other preferred indicators are phenylenediamine or indophenol derivatives. Phenylenediamine-immonium salts are particularly preferred among these. The most preferred of these compounds are:

(V)

Nile blue A

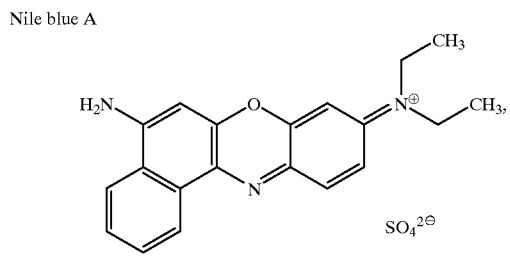

thionine acetate (VI)

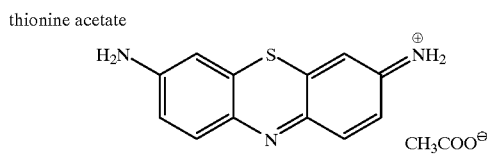

and 2,6-dichlorophenol indophenol as well as its salts (VII)

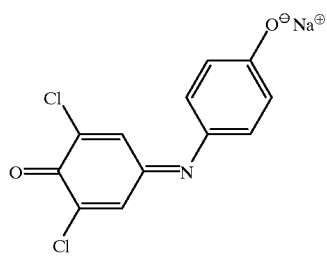

The compounds that can be used according to the present invention have high stability in a strongly oxidizing matrix, which is especially advantageous for systems in which the indicator is in prolonged contact with the oxidizing reagents. As a result, the storage stability of such compounds is advantageously increased. Other advantages that arise from the use of the indicators according to the present invention are the lowering of the detection limit and the reduction in the necessary number of strokes in detector tubes, the possibility of using oxidizing agents that display only a slight change in color during the reaction process (this is possible because the indicators do not depend on the reagent, but depend only on the current redox potential), as well as the reduction in the necessary amount of toxic oxidizing agents, e.g., chromate.

The benzidine derivatives used according to the present invention surprisingly additionally have improved storage stability, especially under oxidative conditions, against all the other compounds mentioned.

The determination of the gas and/or vapor components of a gas mixture is preferably performed in detector tubes. The detector tubes comprise a glass tube, on the inner space of which fine-grained carrier material is fixed. For example, silica gel, quartz glass, aluminum oxide or plastic may be used as the carrier material. The oxidizing reagents and the redox indicator are applied in very thin layers to the carrier material.

It is also possible to apply a plurality of layers of different chemical reactivities within the same tube, e,g., in order to change an analyte in a preceding layer chemically such that it can be detected with a color reaction in a layer following that layer.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a view of a testing element with a carrier having material applied thereto according to the examples of the invention.

DESCRIPTION OF THE PREFERRED EMBODIMENTS

Referring to the drawings in particular, the only FIGURE shows a testing element generally designated 10 with a detector tube 12 that contain carrier materials 14, to which the oxidizing reagents and redox indicators are applied according to the following examples of the invention.

EXAMPLES

Example 1

Synthesis of N,N'-Bis[2,3,5,6-tetrafluoro-4-(trifluoromethyl)-phenyl]-benzidine

A mixture of benzidine (10 mmoles, 1.84 g), octafluorotoluene (20 mmoles, 4.60 g), pyridine (20 mmoles, 1.58 g), and 40 mL of DMSO were stirred for 4 hours at 100° C. The solution was then cooled to room temperature, charged into 0.5% aqueous hydrochloric acid (100 mL), extracted with methylene chloride (4×50 mL), and dried over $Na_2SO_4$. The solvent was drawn off via a silica gel column and the rest was recrystallized from toluene/heptane (1:1, v/v). Yield: 1.1 (18%), melting point 179–180.5° C.

Example 2

Reduction of the Chromate Concentration in Detector Tubes

The Alco-Check™ detector tube currently being used is yellow due to the coating with chromate(VI). The color changes to green in the presence of ethanol. If the chromate is reduced to one twentieth of the original quantity, the yellow color is no longer perceptible to the naked eye. If the redox indicator from Example 1 was added, the color of the detector tube changed to deep pink. The addition of small amounts of ethanol then led to colorization.

The preparation thus prepared was about 10 times more sensitive than the detector tubes currently known.

As an alternative, the preparation is colored reddish brown by Nile blue (5 mg); the chromate reagent turns yellow on contact with ethanol or methanol.

As an alternative, thionine acetate (5 mg) is used as the indicator, the preparation turns green; the chromate reagent turns blue on contact with alcohol.

As an alternative, using sodium salt of 2,6-dichlorophenol indophenol (5 mg) as the indicator, the color of the preparation is reddish purple, changing to light purple on contact with alcohol.

Example 3

Detector Tubes with Silica Gel as the Carrier Material

Twenty g of wide-pored silica gel of a particle size of 0.3–0.4 mm is mixed with 100 mg of potassium dichromate and 2.5 mL of concentrated sulfuric acid. The color of the preparation is a very faint yellow. The color of the reagent changes to deep pink by the addition of 10 mg of N,N'-bis[2,3,5,6-tetrafluoro-4-(trifluoromethyl)-phenyl]-benzidine. The preparation thus prepared becomes decolorized upon the addition of ethanol vapor.

Example 4

Detector Tubes with Quartz Glass as the Carrier Material 0.15 mL of a potassium dichromate solution in concentrated sulfuric acid (0.05 g of potassium dichromate in 50 mmoles of 100% sulfuric acid) are added to 50 g of coarse quartz glass particles and briefly shaken intensely. Then, $1.5 \cdot 10_{-6}$ moles (0.8 mg) of N,N'-bis[2,3,5,6-tetrafluoro-4-[()trifluoromethyl)-phenyl]-benzidine are added and shaken intensely for 20 minutes. The preparation turns deep pink and reacts with alcohols, such as methanol or ethanol, while decolorizing.

While specific embodiments of the invention have been shown and described in detail to illustrate the application of the principles of the invention, it will be understood that the invention may be embodied otherwise without departing from such principles.

What is claimed is:

1. A process for using a testing element, comprising the steps of:

providing a testing element with a carrier material, at least one oxidizing agent applied to said carrier material and at least one redox indicator applied to said carrier material, wherein said redox indicator is in the oxidized form and is storage stable under oxidizing conditions, and is selected from the group consisting of a phenylene diamine derivative, an indophenol derivative and a benzidine derivative; and determining oxidizable gas and/or vapor components in a gas mixture with said testing element.

2. The process of claim 1 wherein said step of determining oxidizable gas and/or vapor components consists of determining alcohols, gasoline hydrocarbons and/or carbon monoxide.

3. A testing element for the colorimetric determination of oxidizable gas and/or vapor components in a gas mixture, the element comprising:

a carrier material;

at least one oxidizing agent applied to said carrier material; and at least one redox indicator applied to said carrier material, wherein said redox indicator is in the oxidized form and is a phenylenediamine-immonium salt.

4. A testing element for the colorimetric determination of oxidizable gas and/or vapor components in a gas mixture, the element comprising:

a carrier material;

at least one oxidizing agent applied to said carrier material; and at least one redox indicator applied to said carrier material, wherein said redox indicator is in the oxidized form and is a benzidine derivative according to the formula in which the radicals R are identical or different and denote a hydrogen, alkyl, aryl, halogen, trifluoromethyl, cyano, nitro, dialkylamino, ester, sulfoxyl ester, alkyloxy or aryloxy; x denotes a halogen; Y denotes a trifluoromethyl, cyano, nitro, dialkylamino, ester, sulfoxyl ester, alkyloxy or aryloxy; n is an integer ranging from zero to three; and m equals 5−n.

5. The testing element of claim 4 wherein all radicals R in formula (I) are identical and each denotes a hydrogen.

6. The testing element of claim 4 wherein x in formula (I) denotes fluorine.

7. The testing element of claim 4 wherein n in formula (I) equals 1 and m equals 4.

8. A process for using a testing element, comprising the steps of:

providing a testing element with a carrier material, at least one oxidizing agent applied to said carrier material and at least one redox indicator applied to said carrier material, wherein said redox indicator is in the oxidized form and is a phenylenediamine-immonium salt; and determining oxidizable gas and/or vapor components in a gas mixture with said testing element.

9. A process for using a testing element, comprising the steps of:

providing a testing element with a carrier material, at least one oxidizing agent applied to said carrier material and at least one redox indicator applied to said carrier material, wherein said redox indicator is in the oxidized form and is a benzidine derivative according to the formula

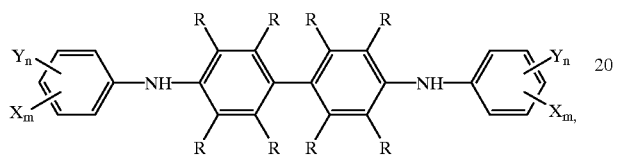

(I)

in which the radicals R are identical or different and denote a hydrogen, alkyl, aryl, halogen, trifluoromethyl, cyano, nitro, dialkylamino, ester, sulfoxyl ester, alkyloxy or aryloxy; x denotes a halogen; Y denotes a trifluoromethyl, cyano, nitro, dialkylamino, ester, sulfoxyl ester, alkyloxy or aryloxy; n is an integer ranging from zero to three; and m equals 5−n; and determining oxidizable gas and/or vapor components in a gas mixture with said testing element.

10. A testing element for the colorimetric determination of oxidizable gas and/or vapor components in a gas mixture, the element comprising:

a carrier material;

at least one oxidizing agent applied to said carrier material;

at least one redox indicator applied to said carrier material, wherein said redox indicator is in the oxidized form and is storage stable under oxidizing conditions, and is selected from the group consisting of a phenylene diamine derivative, an indophenol derivative and a benzidine derivative; and wherein said redox indicator is Nile blue A.

11. A testing element for the calorimetric determination of oxidizable gas and/or vapor components in a gas mixture, the element comprising:

a carrier material;

at least one oxidizing agent applied to said carrier material;

at least one redox indicator applied to said carrier material, wherein said redox indicator is in the oxidized form and is storage stable under oxidizing conditions, and is selected from the group consisting of a phenylene diamine derivative, an indophenol derivative and a benzidine derivative; and wherein said redox indicator is thionine acetate.

12. A testing element for the colorimetric determination of oxidizable gas and/or vapor components in a gas mixture, the element comprising:

a carrier material;

at least one oxidizing agent applied to said carrier material;

at least one redox indicator applied to said carrier material, wherein said redox indicator is in the oxidized form and is storage stable under oxidizing conditions, and is selected from the group consisting of a phenylene diamine derivative, an indophenol derivative and a benzidine derivative; and wherein said redox indicator is 2,6-dichlorophenol indophenol or a salt thereof.

* * * * *